(12) United States Patent
Derbyshire et al.

(10) Patent No.: US 6,452,401 B1
(45) Date of Patent: Sep. 17, 2002

(54) CHARGED PARTICLE ANALYSIS

(76) Inventors: Gareth Derbyshire, Barrow Lane, Harwell, Oxfordshire OX11 0FA (GB); Edmond J. Bateman, The Orchard, Badswell Lane, Appleton Abingdon, Oxfordshire OX13 5LF (GB)

( * ) Notice: Subject to any disclaimer, the term of this patent is extended or adjusted under 35 U.S.C. 154(b) by 0 days.

(21) Appl. No.: 09/367,446
(22) PCT Filed: Feb. 3, 1998
(86) PCT No.: PCT/GB98/00348
§ 371 (c)(1), (2), (4) Date: Nov. 29, 1999
(87) PCT Pub. No.: WO98/36268
PCT Pub. Date: Aug. 20, 1998

(30) Foreign Application Priority Data

Feb. 14, 1997 (GB) .............................. 9703024

(51) Int. Cl.⁷ .............................. G01N 27/62
(52) U.S. Cl. .................. 324/464; 324/459; 324/452
(58) Field of Search .................. 324/452, 455, 324/459, 464, 467

(56) References Cited

U.S. PATENT DOCUMENTS

| | | | |
|---|---|---|---|
| 4,652,866 A | * 3/1987 | Siegmann et al. | 324/464 X |
| 5,038,043 A | 8/1991 | Dorion et al. | |
| 5,254,861 A | * 10/1993 | Carpenter et al. | 324/464 X |
| 5,584,938 A | * 12/1996 | Douglas | 324/459 X |

FOREIGN PATENT DOCUMENTS

| | | |
|---|---|---|
| EP | 0350874 | 1/1990 |
| EP | 0368694 | 5/1990 |

OTHER PUBLICATIONS

OED, "Position–Sensitive Detector With MicroStrip Anode For Electron Multiplication With Gases," Nuclear Instruments and Methods in Physics Research A263 (1988) 351–359, © Elsevier Science Publishers B.V.

* cited by examiner

*Primary Examiner*—Glenn W. Brown
(74) *Attorney, Agent, or Firm*—Akin, Gump, Strauss, Hauer & Feld, LLP

(57) ABSTRACT

A detection device for analyzing charged particles. The charged particle analyzer comprises a source of charged particles and a charged particle detector spaced from the source and immersed within the source in an ionizable gas. The detector comprises at least one pair of electrodes, characterized in that the electrodes of the pair are spaced apart by a distance that is substantialy less than the spacing between the source and detector. The electrodes of the pair are maintained at different potentials, and the source is maintained at a potential different from the potentials of the electrodes. The potentials are selected such that charged particles emitted by the source are attracted from the source toward each of the pair of electrodes and such that charged particles adjacent the detector are accelerated to energies sufficient to ionize the gas.

11 Claims, 2 Drawing Sheets

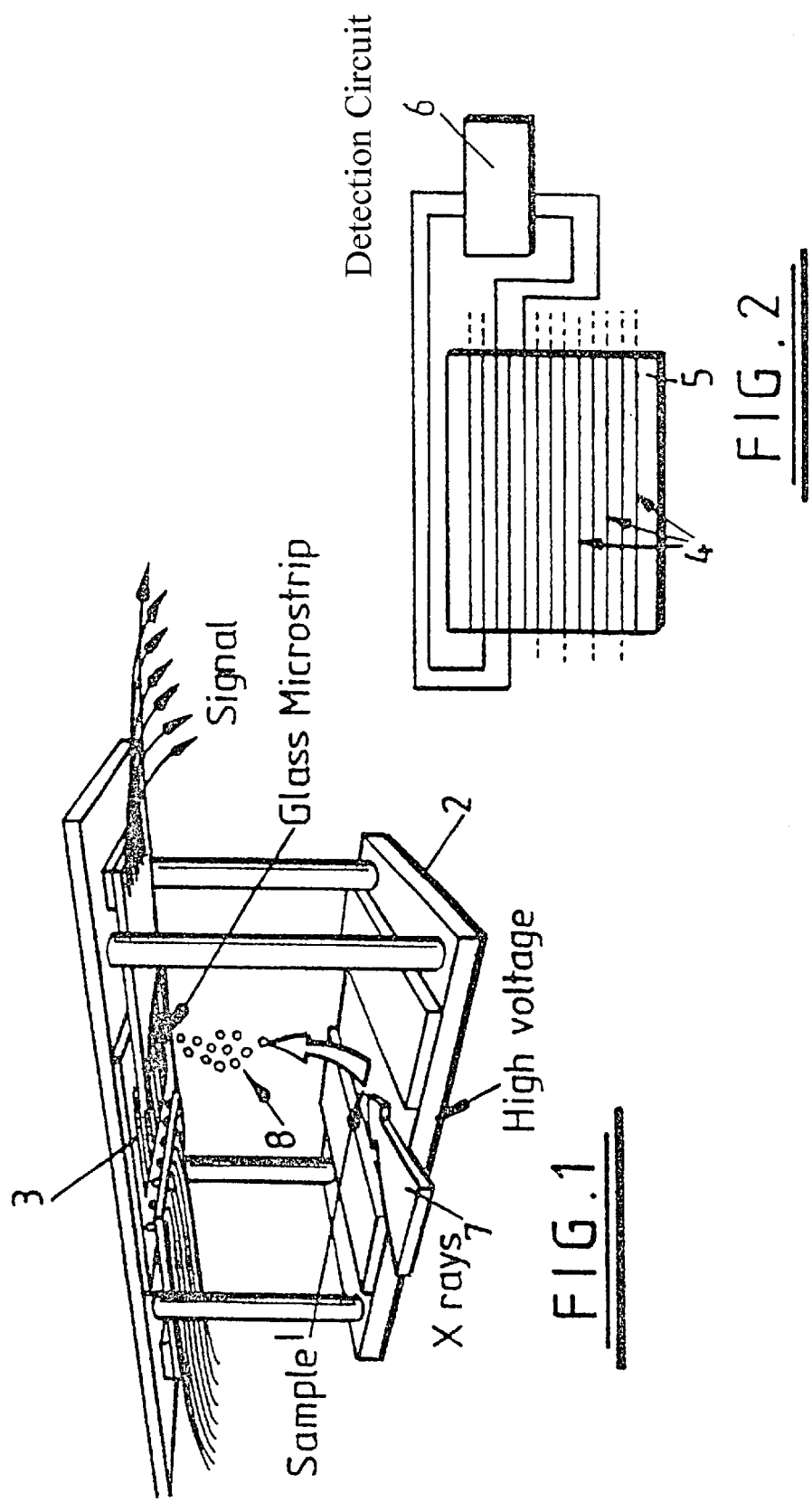

CHARGED PARTICLE ANALYSIS

BACKGROUND OF THE INVENTION

This invention relates to an apparatus and method for analyzing charged particles.

Measurement of electron yield is a known technique which is used to study the response of material surfaces to interactions with beams of high energy photons such as X-rays. Exposing a surface of a material to X-rays of varying energies, and measuring the number and energy of electrons emitted from the surface, makes it possible to analyze the chemical characteristics of the surface in detail.

A known method of measuring electron yield involves placing a sample in a high vacuum environment, exposing the sample to a beam of X-rays, and detecting a total electron yield current at a collection plate. The sample is held at a negative voltage relative to the collection plate to promote the drift of electrons from the sample to the collection plate. A variation of this method is to use a gas filled ion chamber, where the electron yield is measured indirectly as part of a total current from the sample. There is no overall gain employed in either of these methods, and the currents measured should correspond exactly to the number of electrons which leave the sample. These currents are small and are consequently prone to distortion by 'pick-up' and 'leakage' in the local environment. A method of obtaining noise free or close to noise free gain of the current of electrons emitted from the sample surface would significantly enhance the sensitivity of the electron yield measurement.

One approach to providing an increased sensitivity of electron yield has been to hold the sample in a high vacuum environment, and use an electron multiplier (such as a microchannel plate). However, useful samples are not ideal for high vacuum systems and a method of measurement which could operate at atmospheric pressure would be much more useful. The possibility of obtaining chemical reactions on the surface of the sample must also be considered. To this end, an alternative approach to measuring electron yield has been devised, wherein a sample and detector are surrounded with a gas mixture. The gas mixture is chosen such that, under the appropriate conditions, an electron emitted from the sample surface will ionize gas molecules, thereby forming an electron cloud in the gas. The number of electrons in the cloud will be equal, within statistical limits, to the energy of the initial electron divided by the ionization energy of the gas.

The electron cloud is subsequently accelerated along a radial field radiating from a wire anode. The electrons accelerate until they acquire sufficient energy to cause fisher ionization of the gas molecules, thereby creating more electrons, which are accelerated and ionize further electrons, in what is known as an avalanche effect. The strength of the field at the wire is limited so that the number of electrons produced by the ionization is proportional to the number of electrons in the cloud formed at the surface of the sample.

Since only a single wire is used to detect electrons, the detection system is only capable of measuring the total number of electrons arriving at the wire in any given time interval, and does not provide any spatial information. More specifically, the wire detection system does not allow a user to determine from what position on the surface of a sample electrons have been emitted.

It is an object of the present invention to overcome or substantially mitigate the above disadvantages.

SUMMARY OF THE INVENTION

According to the invention there is provided a charged particle analyzer comprising a source of charged particles and a charged particle detector spaced from the source and immersed with the source in an ionizable gas, wherein the detector comprises at least one pair of electrodes which are spaced apart by a distance that is substantially less than the spacing between the source and detector, the electrodes of the pair are maintained at different potentials, and the source is maintained at a potential different from the potentials of the electrodes, the potentials being selected such that charged particles emitted by the source are attracted from the source towards each of the pair of electrodes, and such that charged particles adjacent the detector are accelerated to energies sufficient to ionize the gas.

If the charged particles are negatively charged, the source is held at a potential which is more negative than the potentials of both the electrodes of the pair.

Preferably, the source is a sample and means are provided for exposing the sample to a beam of radiation the energy of which is sufficient to cause charged particles to be emitted from the sample. The exposing means may comprise an X-ray source. The sample may define a surface which is substantially planar and the beam may be directed towards the sample in a direction inclined to a normal to the sample surface. The beam may be directed at a glancing angle relative to the sample surface.

Suitably, the energy beam is monoenergetic and the energy of the beam is varied with time to provide analysis over a range of energies.

Suitably, the energy of the beam is non-uniform such that the incident energy varies across an area of the sample irradiated by the beam, and the electrodes are positioned to receive charged particles form different portions of that area, the incident energy varying between said portions.

The electrodes are preferably defined by parallel strips of conductive material mounted on an semiconducting substrate. The electrodes of the pair may be located so as to be substantially equidistant from the source.

The invention also provides a method for analyzing charged particles emitted by a source, wherein the source and a charged particle detector are immersed in an ionizable gas, the detector being provided with at least one pair of electrodes, characterized in that the electrodes of the pair are spaced apart by a distance substantially less than the distance between the source and the detector, different potentials are applied to the electrodes, and the source is maintained at a potential different from the potentials of the electrodes, the potentials being selected such that charged particles emitted by the source are attracted from the source towards each of the pair of electrodes, and such that charged particles adjacent the detector are accelerated to energies sufficient to ionize the gas.

BRIEF DESCRIPTION OF THE DRAWINGS

Specific embodiments of the present invention will now be described by way of example only with reference to the accompanying drawings, in which:

FIG. 1 is a schematic perspective view of a charged particle analyzer according to a first embodiment of the invention;

FIG. 2 is a schematic view of a detector incorporated in the analyzer of FIG. 1.

DETAILED DESCRIPTION

Figure 3:
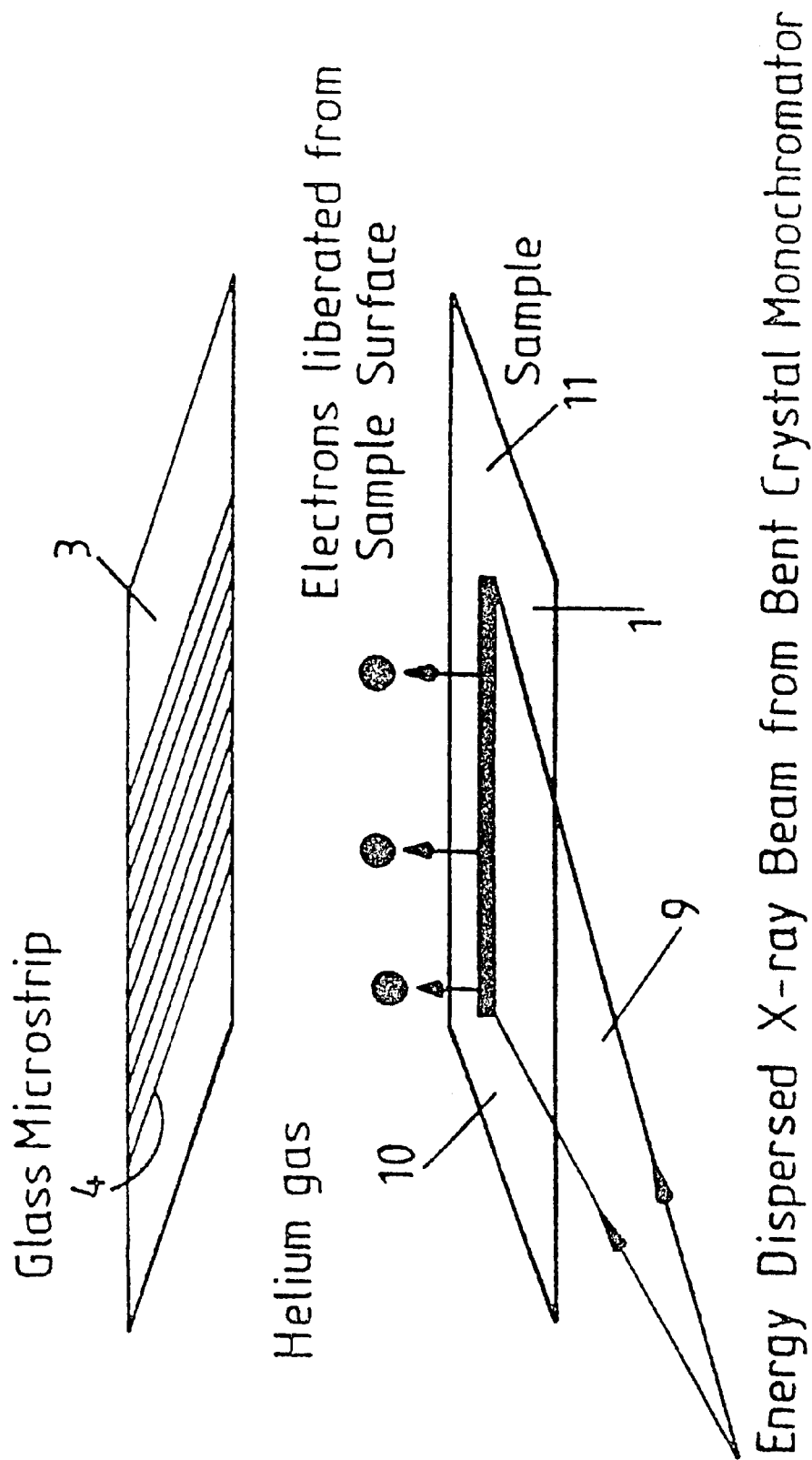
FIG. 3 is a schematic perspective view of a second embodiment of the invention.

Referring to FIG. 1, a sample 1 is positioned on a planar base 2. A detector 3 is provided directly above the sample 1 and the base 2. The detector 3 is planar, and lies in a plane which is parallel to the plane of the sample 1 and the base 2.

The detector 3, shown in more detail in FIG. 2, comprises a series of parallel electrodes 4 deposited onto a semiconducting glass plate 5. Alternate electrodes 4 on the microstrip are held at positive and negative relative voltages, to provide a pattern of anodes and cathodes. The electrodes 4 are each of equal width, and lithographic techniques may be used to produce electrodes 4 as little as 10 microns wide. Each electrode is connected to a detection circuit 6 which monitors the electrical signal from that electrode 4.

The base 2 and sample 1, shown in FIG. 1, are held at a constant potential which is more negative than the potential of the negative electrodes 4 of the detector 3, so that all of the electrodes 4 of the detector 3 are at a positive potential relative to the base 1 and sample 2.

The sample 1 and detector 3 are held in a sealed chamber (not shown) which is filled with gas which is predominantly Helium. The gas may also contain a quenching gas such as Isobutane, typically at a level of around 10 per cent, which acts to stop continuous electrical breakdown in the atmosphere.

In use, X-rays are generated using a synchrotron or other means (not shown), and X-rays with a desired energy are selected from the synchrotron and directed as a beam 7 onto the surface of the sample 1. The X-rays approach the sample 1 from a direction which is perpendicular to the orientation of the electrodes 4 on the detector 3. The angle formed between the beam of X-rays 4 and the surface of the sample 1 is small, so that the X-rays impinge on the surface of the sample 1 at a glancing angle. The area on the surface of the sample 1 onto which the X-rays impinge is varied by changing the angle between the X-rays and the sample 1. The X-rays have little interaction with the predominantly Helium gas, and variation of the angle of the X-rays in this way does not lead to spurious results.

Electrons at the surface of the sample 1 acquire energy from the X-ray beam 7, and are emitted from the sample 1. In a first preferred arrangement, the energy of the X-rays is chosen to be just greater than the energy needed to cause emission of the electrons, so that once emitted the electrons have a limited amount of kinetic energy, and will not tend to drift far from the position at which they left the surface of the sample 1. The energy of the emitted electrons and the electric field from the detector 3 close to the sample 1 is not sufficient for the electrons to cause ionization of the gas close to the sample 1 surface.

In a second preferred arrangement, the energy of the X-rays is chosen to be sufficient such that electrons emitted from the sample 1 cause limited ionization of the gas, leading to the formation of localized clouds of electrons at the surface of the sample 1. Each cloud of electrons is proportional in number of electrons to the energy of an electron ejected from the surface of the sample 1.

In a third preferred arrangement, the density of the gas is chosen to be low so that ionization interactions with the gas are spread throughout the gas as the electrons travel towards the microstrip detector 3.

In general, the pressure of the gas, the voltage gradient through which the electrons pass, and the initial kinetic energy of the electrons determine whether the initial interactions of electrons with the gas are close to the surface of the sample 1 or spread throughout the gas as the electrons travel towards the detector 3. The pressure of the gas and the voltage maintained at the detector 3 may be optimized to measure position or energy resolution of an electron emitted form the sample 1.

The positive voltage of the sample 1 and base 2, relative to the detector 3, causes each electron cloud to drift towards the detector 3 (the drifting electrons are shown as 8 in FIG. 1). Information relating to the position at which the electrons were emitted from the sample 1 is retained during drift of the electron cloud since the direction of drift is perpendicular to the surface of the sample 1, and the electrons do not have sufficient kinetic energy to deviate significantly from a position directly above the point from which they were emitted.

The pattern of parallel anodes and cathodes 4 provided on the detector 3 does not affect the drift of the electron cloud until it is immediately adjacent the detector 3. This is because the electric field produced as a consequence of the close proximity of the anodes and cathodes 4 on the detector 3 is very localized. As the electrons approach the detector 3, they are accelerated towards the anodes by the localized electric field, whose intensity increases rapidly adjacent the detector 3. The acceleration of the electrons provides them with sufficient energy to ionize the gas in the chamber, producing more electrons which themselves cause further ionization. In this way, the electrons emitted form the sample 1 produce an avalanche of electrons from the gas adjacent the detector 3. The generation of an avalanche of electrons is useful because it increases the electrical signal produced at the detector 3 to a level which may be accurately measured. The gain in signal produced by the avalanche is controlled to ensure that the final number of electrons detected is proportional to the initial number of electrons emitted from the sample 1.

Localizing the avalanche of electrons in a region immediately adjacent the detector 3 is advantageous because the electrons produced by ionization of the gas remain localized, and spatial information relating to the electrons emitted form the sample 1 is retained. The spatial information referred to is simply the position at which electrons were emitted from the sample relative to a front and a back end of the sample 1.

The front and back ends of the sample 1 are defined as being the ends of the sample 1 which are nearest and furthest respectively from the origin of the X-ray beam 7. The relative strength of the signals received from each of the electrodes 4 on the detector 3 is used to identify the point at which the X-ray beam 7 interacted with the surface of the sample 1.

The energy of the X-ray beam 7 incident on the sample 1 may be chosen to be considerably greater than the energy needed to emit electrons from the sample 1. If so, electrons produced from the sample 1 will retain considerable energy after liberation, and will cause ionization of the atmosphere above the sample 1. A cloud of electrons 8 whose number is derived form the excess energy of the X-ray beam 7 will be formed, and will drift towards the detector 3 as described above. This mode of operation substantially limits the spatial information relating to electrons which were emitted from the surface of the sample 1.

An alternative mode of operation of the invention, depicted schematically in FIG. 3, allows the simultaneous measurement of the response of a sample 1 to X-rays at different energies. In this mode of operation, rather than using X-rays with a narrow energy band, a broader band of energies is used (for example 8 keV to 9 keV). The selected X-rays are directed through a silicone crystal (not shown), which refracts the X-rays through an angle determined by their energy, to produce a fan of X-rays 9 at different energies. The orientation of the X-ray fan 9 is such that the energy of the X-rays incident on the sample 1 is greatest at one end 10 of the sample 1, and decreases linearly to a minimum at the opposite end 11 of the sample 1.

The energy of the X-ray fan 9 may be chosen so that emitted electrons have insufficient energy to cause ionization of the gas close to the surface of the sample 1. Alternatively, the X-rays may be chosen to be sufficiently energetic that electrons emitted from the surface of the sample 1 will have some limited energy, and will form a localized electron cloud adjacent the positions on the sample 1 from which they were ejected. The electron cloud will have a total charge which is proportional to the energy of the ejected electron.

The localized electron cloud will be attracted to the detector 3 as described above, and will cause localized avalanches of electrons adjacent the electrodes 4 of the detector 3. Measurement of the electrical signal at each of the anodes 4 of the detector 3 will allow the calculation of the number of electrons produced at different positions on the surface of the sample, and will therefore provide a measurement of the response of different parts of surface of the sample 1 to different energies of X-rays. This mode of operation is most advantageous since it allows an X-ray absorption profile of a sample 1 over a range of X-ray energies to be determined in a single 'parallel' measurement, with consequent savings in experimental time and the elimination of experimental errors caused by variations over time of equipment settings.

The strength of the electric field adjacent the detector 3 is determined by the potentials applied to the anodes and cathodes 4 of the detector 3, and also by the distance between them. Reducing the spacing between the anodes and cathodes will increase the gradient of the electric field adjacent the detector 3, and the applied potential needed to produce a desired acceleration of electrons will be correspondingly reduced. Increasing the density of electrodes 4 on the detector 3 will also increase the spatial resolution of the detector 3.

Although the above embodiments refer solely to the detection of electrons, it should be understood that the invention may be used for the detection of other positively or negatively charged particles.

The use of a predominantly Helium gas, as described above, is advantageous since X-rays that are scattered from the sample 1, and emitted from deep within the sample 1, have very little interaction with the Helium gas. These X-rays are not seen by the detector, and therefore do not swamp the detector with information about structure deep within the sample. Thus, the system is essentially X-ray blind, and the sensitivity of the surface electron detection is not comprised.

What is claimed is:

1. A charged particle analyzer comprising a source of charged particles and a charged particle detector spaced from the source and immersed with the source in an ionizable gas, the detector comprising at least one pair of electrodes, characterized in that the electrodes of the pair are spaced apart by a distance that is substantially less than the spacing between the source and detector, the electrodes of the pair are maintained at different potentials, and the source is maintained at a potential different from the potentials of the electrodes, the potentials being selected such that charged particles emitted by the source are attracted from the source towards each of the pair of electrodes and such that charged particles adjacent the detector are accelerated to energies sufficient to ionize the gas.

2. An analyzer according to claim 1, wherein the charged particles are negatively charged, and the source is held at a potential which is more negative than the potentials of both the electrodes of the pair.

3. An analyzer according to claim 1, wherein the electrodes are defined by parallel strips of conductive material mounted on a semiconducting substrate.

4. An analyzer according to claim 1, wherein the electrodes of the pair are located so as to be substantially equidistant from the source.

5. An analyzer according to claim 1, wherein the source is a sample and means are provided for exposing the sample to a beam of radiation the energy of which is sufficient to cause charged particles to be emitted from the sample.

6. An analyzer according to claim 5, wherein the exposing means comprises an X-ray source.

7. An analyzer according to claim 5, wherein the sample defines a surface which is substantially planar and the beam is directed at a glancing angle relative to the sample surface.

8. An analyzer according to claim 5, wherein the sample defines a surface which is substantially planar and the beam is directed towards the sample in a direction inclined to a perpendicular to the sample surface.

9. An analyzer according to claim 8, wherein the energy of the beam is non-uniform such that the incident energy varies across an area of the sample irradiated by the beam, and the electrodes are positioned to receive charged particles from different portions of the area of the sample, the incident energy varying between said portions.

10. An analyzer according to claim 8, wherein the energy of the beam is uniform.

11. A method for analyzing charged particles emitted by a source, wherein the source and a charged particle detector are immersed in an ionizable gas, the detector being provided with at least one pair of electrodes, characterized in that the electrodes of the pair are spaced apart by a distance substantially less than the distance between the source and the detector, different potentials are applied to the electrodes, and the source is maintained at a potential different from the potentials of the electrodes, the potentials being selected such that charged particles emitted by the source are attracted from the source towards each of the pair of electrodes and such that charged particles adjacent the detector are accelerated to energies sufficient to ionize the gas.

* * * * *